(12) United States Patent
Teal et al.

(10) Patent No.: US 8,092,789 B1
(45) Date of Patent: Jan. 10, 2012

(54) INDIAN MEAL MOTH ATTRACTANT

(75) Inventors: Peter E. A. Teal, Gainesville, FL (US); Don L. Silhacek, Gainesville, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 205 days.

(21) Appl. No.: 12/362,236

(22) Filed: Jan. 29, 2009

(51) Int. Cl.
*A01N 25/00* (2006.01)
*A01N 27/00* (2006.01)
*A01N 31/02* (2006.01)
*A01N 35/00* (2006.01)
*A01N 43/08* (2006.01)
*A01P 19/00* (2006.01)

(52) U.S. Cl. .......... 424/84; 514/461; 514/693; 514/724; 514/762; 514/772

(58) Field of Classification Search .................. None
See application file for complete search history.

(56) References Cited

OTHER PUBLICATIONS

Buttery et al. "Raisin and Dried Fig Volatile Components: Possible Insect Attractants" in:Teranishi et al., Qualtiy of Selected Fruits and Vegetables of North America (1981). pp. 29-41.*
Napasol, The Indian meal moth *Plodia interpunctella* (2007).*
Sjovall et al., J. Agric. Food Chem. (2000), vol. 48, pp. 3522-3527.*

* cited by examiner

*Primary Examiner* — Johann Richter
*Assistant Examiner* — Frank Choi
(74) *Attorney, Agent, or Firm* — John D. Fado; Robert D. Jones

(57) ABSTRACT

A composition containing undecane, hexanal, 1-pentanol, decane, and 2-pentylfuran is an effective attractant for adult female Indian meal moths (*Plodia interpunctella*). The composition may be used alone or with a carrier component. The composition may be used in combination with any insect trapping means known in the art, as required for a specific application.

9 Claims, 4 Drawing Sheets

INDIAN MEAL MOTH ATTRACTANT

FIELD OF THE INVENTION

The present invention relates to an attractant for Indian meal moths. Specifically, the invention relates to an attractant for adult female moths.

BACKGROUND OF THE INVENTION

The Indian Meal Moth (*Plodia interpunctella*) is the most serious and wide spread moth pest of stored grains and grain products in the world. The pest has a huge economic impact on grain storage warehouses, as well as milling, packaging, and consumer-visited facilities (e.g. grocery stores, pet food markets, etc.).

In commercial facilities, the moths are controlled through fumigation with Methyl Bromide. However, this method of control is generally untenable at consumer visited facilities. Further, the future availability of Methyl Bromide is suspect and there is currently no substitute approved for wide spread use. Additionally, the application of chemical pesticides directly to harvested food products is generally undesirable.

The need exists for means of controlling the Indian Meal Moth that does not require the application of chemical pesticides. The current invention provides a means of attracting adult female meal moths to a variety of traps and thereby controlling the moth population.

SUMMARY OF THE INVENTION

The current invention is directed to a composition comprising undecane, hexanal, 1-pentanol, decane, and 2-pentylfuran and mixtures thereof, and a carrier or carrier material serving as a slow release system. The composition is primarily used as an attractant for adult female Indian meal moths.

The current invention is also directed to a method of attracting adult female Indian mean moths. The method includes treating an area or object with an effective amount of Indian meal moth attractant so that the Indian meal moths are drawn to the area or object. The attractant of the current invention comprises undecane, hexanal, 1-pentanol, decane, and 2-pentylfuran and mixtures thereof. The attractant may be used alone or with a carrier.

DETAILED DESCRIPTION OF PREFERRED EMBODIMENTS

Figure 1:
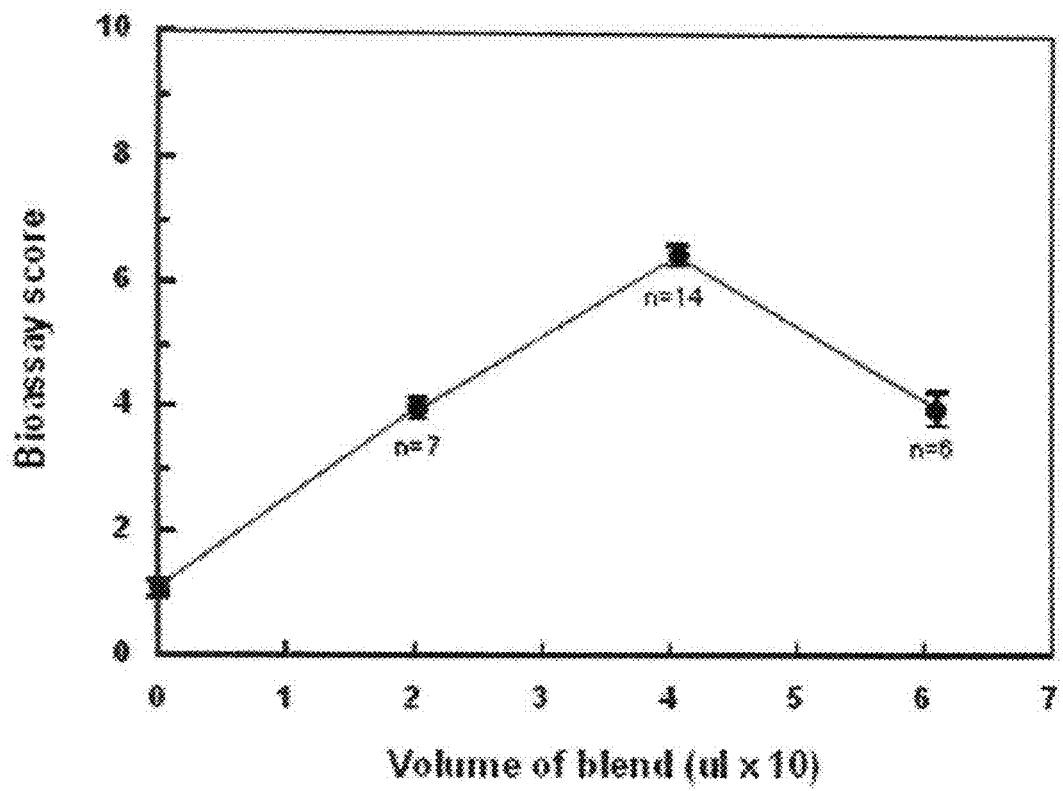
FIG. 1. Dilutions of Blend EI were bioassayed (error indicated is standard error).

Food attractants for stored product pests have generally not received as much attention as have sex attractants. In the cases where food attractants have been used, the attractant has generally comprised the food itself or a specific part of the food thought to be desirable. The exact chemical source of the attractant has not been identified, and therefore the specific chemical attractant has not been concentrated or otherwise manipulated to increase the attractant's efficiency or effectiveness.

As indicated infra, the inventors tested a variety of potential attractants for female Indian meal moth (*Plodia interpunctella*). The inventors found that a blend of synthetic chemicals designated "BlendEI" yielded the best results. BlendEI is comprised of 23.9 ul undecane (Sigma), 9.61 ul hexanal (Sigma), 4.09 ul 1-pentanol (Sigma), 1.78 ul decane (Chemical Samples Co., Columbus, Ohio) and 1.30 ul 2-pentylfuran (Sigma) in 1000 ul dichloromethane.

BlendEI performed almost as well as wheat bran in laboratory tests. However, as compared (on a gram for gram basis) with wheat bran, much smaller quantities of BlendEI are required to function as an attractant, and the BlendEI continues to attract insects long after the attraction to an individual sample of wheat bran has faded.

The BlendEI attractant may be used alone or with a carrier component. Multiple suitable carriers are well-known in the art and may be selected in accordance with a specific application and the needs of a particular user. The carrier component may be comprised of a variety solids or liquids (or combinations thereof) consistent with the function of stabilizing the attractant and facilitating dispersion. The carrier component should function so that BlendEI vapors are emitted to attract the adult female *Plodia*.

Similarly the attractant and carrier may be directly dispersed as a spray or simply exposed to the air in an open container. The attractant and carrier maybe dispersed in combination with various types of substrates and dispersal means including simple membranes, hollow fibers, microcapsules, cigarette filters, gels, polymers, septa, or the like. All of these substrates have been used to release insect attractants in general and should be considered within the scope of the invention. The carrier should function so that BlendEI vapors are emitted to attract the *Plodia* adults.

The attractant may be used in combination with any compatible insect trap known in the art so that the insects are killed or captured. The most common trap comprises an insect lure (such as the current invention) surrounded by sticky surfaces that entrap the insect as the insect approaches the lure. However, all mechanical, electrical, chemical, and biologically-based traps (and combinations thereof) should be considered within the scope of the current invention.

Method

All tests were conducted in a clear, acrylic flight chamber 75 cm (L), 22 cm (W), 24 cm (H). Room air was pushed through the chamber with a 115 volt, 0.35 Amp motor-driven roller fan. Air speed was maintained at 0.4 m/sec. The chamber was positioned horizontally on a table in a walk-in environmental chamber maintained at 30° C. and 65% R.H. The only light was provided by a 25 Watt red filtered incandescent bulb centrally positioned 90 cm above tunnel floor and providing 9.0 Lux at the floor center.

Insects used were laboratory reared *Plodia interpuctella*. Ten 4-day old adult females from a general rearing box were selected and transferred into a 7 dram screened plastic vial for each test. Tests were performed only during the first four hours of the scotophase. Test subjects consisted of either natural products held in a glass Petri dish (Kimax, 5 cm diameter) or liquid volatiles pipetted onto a filter paper disc (Whatman #3, 2.3 cm) held off the floor by a plastic disc (5 cm diameter). These were placed upwind. A test began when the vial containing the moths was placed on the floor down-wind and the lid of the vial was removed. Distance between vial and test material was 62 cm. Female movement was observed for ten minutes and each female was scored on progress upwind: 0.25 for each of three one-quarter floor length lines crossed per female. A final 0.25 was scored for actually contacting the test subject. Individual moths were tested only once.

Volatiles from natural products were collected for twenty-four hours by passing commercial, compressed nitrogen through a 150 $cm^3$ glass collection chamber (Analytical Research Systems) connected by tubing to an inert filter trap of 20 mg SuperQ (Alltech Associates). The collected volatiles were eluted with 150 ul dichloromethane and then bioassayed in the flight tunnel and analyzed by GC-MS. The SuperQ filter traps were rinsed with 200 ul dichloromethane immediately before each use.

Results

Natural products and chemicals were tested for their attractiveness (See Table 1 infra). Wheat bran was selected as a positive control because females were consistently attracted to it. Several of the chemicals that were identified in natural products by GC-MS analysis were bioassayed. No individual chemical was found to be as attractive as wheat bran. The GC-MS analysis of wheat bran volatiles collected for just ten minutes (to resemble an actual bioassay presentation to females) was used to assemble the five most prominent chemicals into a blend. As indicated supra, this synthetic blend (designated "BlendEI") was composed of 23.9 ul undecane (Sigma), 9.61 ul hexanal (Sigma), 4.09 ul 1-pentanol (Sigma), 1.78 ul decane (Chemical Samples Co., Columbus, Ohio) and 1.30 ul 2-pentylfuran (Sigma) in 1000 ul dichloromethane.

TABLE 1

Selective flight tunnel bioassay results for day 22 *Plodia* females

| Test item | Score | error* | n |
|---|---|---|---|
| MeCl plus MeOH TONES cinnamon superQ | 7.75 | 0.50 | 3 |
| superQ of wheat bran; MeCl** | 7.65 | 0.38 | 10 |
| wheat bran | 6.36 | 0.21 | 20 |
| superQ of ground wheat berry | 6.25 | 0.43 | 3 |
| ground brown rice | 6.19 | 0.29 | 4 |
| ground wheat berry | 6.08 | 0.91 | 10 |
| dried hops | 6.04 | 0.45 | 6 |
| wheat germ | 5.70 | 1.03 | 30 |
| cinnamon, TONES, (*Cassia*, freeze-ground) | 5.53 | 1.08 | 10 |
| rice bran | 5.50 | | 2 |
| superQ of wheat germ; MeCl | 4.75 | 1.25 | 3 |
| fresh pears (Bosc) | 4.48 | 1.64 | 10 |
| superQ of TONES cinnamon; MeOH ) | 3.75 | 0.87 | 3 |
| 2-hexanone | 3.63 | 0.22 | 4 |
| hexyl acetate | 3.60 | | 2 |
| superQ of TONES cinnamon; MeCl | 3.50 | 1.09 | 3 |
| ethyl 4-decenoate | 3.50 | 0.25 | 3 |
| Turmeric | 3.33 | 0.22 | 3 |
| a-copaene | 3.07 | 0.47 | 7 |
| trans-2-hexen-1-ol | 3.00 | 0.38 | 3 |
| cymene | 3.00 | | 2 |
| myrcene | 2.95 | 0.29 | 5 |
| methyl octanoate | 2.91 | 0.68 | 3 |
| borneol | 2.83 | | 3 |
| ethyl vanillin | 2.63 | 0.44 | 6 |
| all purpose flour | 2.34 | 0.86 | 8 |
| malted barley, grd | 2.13 | | 2 |
| acetone solvent control filter paper | 1.65 | 0.42 | 5 |
| superQ of wheat bran MeOH (after MeCl) | 1.58 | 1.42 | 3 |
| superQ of wheat germ; MeOH | 1.16 | 0.95 | 3 |
| superQ of wheat berry MeOH (after MeCl) | 1.08 | 1.04 | 3 |
| blank filter paper | 1.04 | 0.08 | 6 |
| MeCl solvent control filter paper | 1.00 | 0.01 | 6 |
| MeOH solvent control filter paper | 1.00 | 0.43 | 3 |

*Standard error

Figure 2:
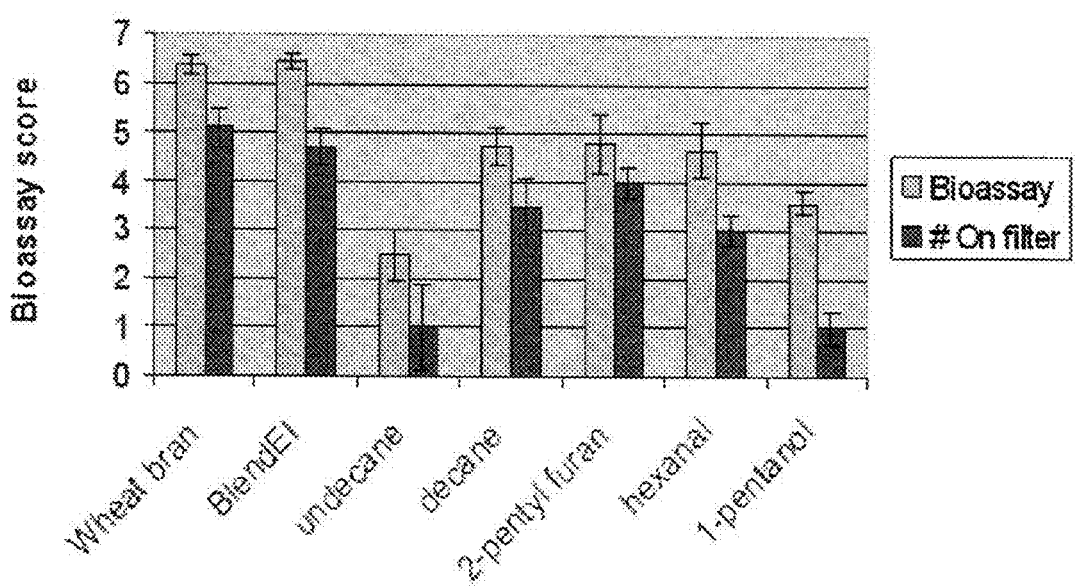
FIG. 2. Blends were prepared deleting one component at a time indicated by label. Samples were bioassayed to measure attraction (three replicates, error bars indicate standard error). The number of females touching the sample filter paper dispenser is also indicated (# on filter). Blend E1 is the 5 component blend; other blends are four component blends from which the compound listed was deleted (undecane=four component blend that did not contain undecane).
Figure 3:
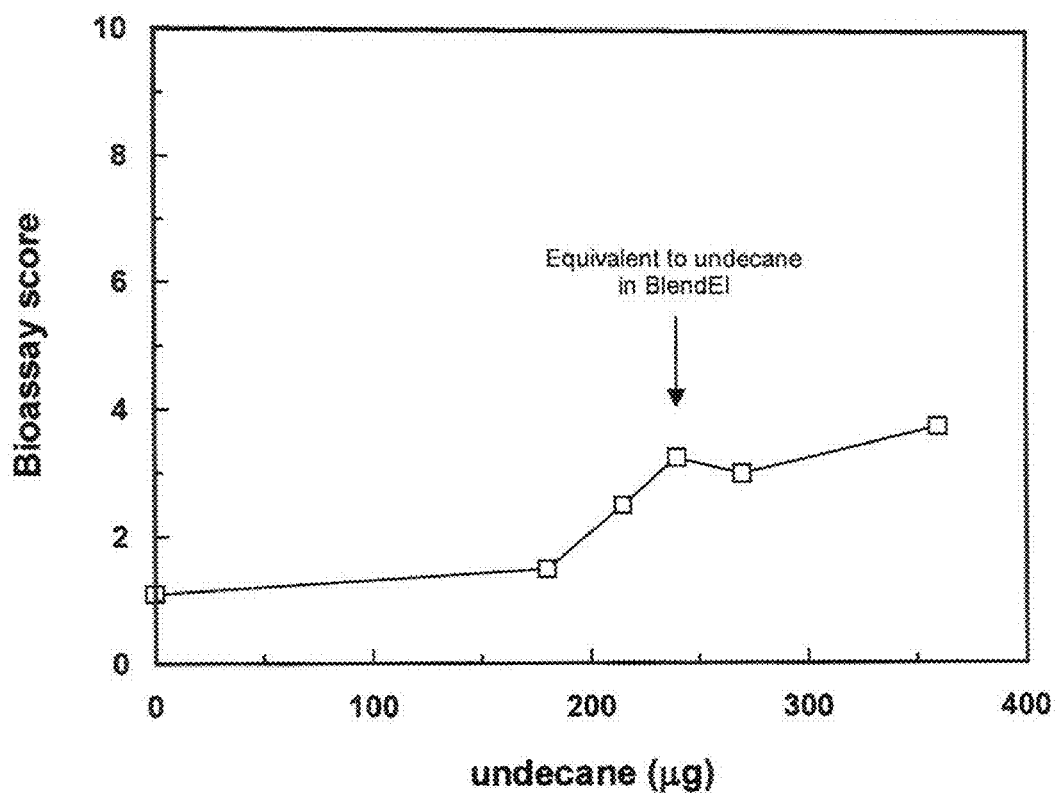
FIG. 3. Dilutions of undecane in dichloromethane were bioassayed.

BlendEI was as attractive as wheat bran when 10 ul in 100 ul dichloromethane was bioassayed (See Table 2 infra). As indicated in FIG. 1, attraction was dependant on dose. Deleting individual components of the blend did not lead to the conclusion that the blend could be simplified (FIG. 2). The most likely component to be able to attract on its own, undecane, was shown to be unattractive alone (FIG. 3). Several other pairings of the components, including undecane and 1-pentanol, did not perform as well as BlendEI (data not shown).

TABLE 2

Selective flight tunnel bioassay results for day 22 *Plodia* females

| Test item | Score | error* | n |
|---|---|---|---|
| MeCl plus MeOH TONES cinnamon superQ | 7.75 | 0.50 | 3 |
| superQ of wheat bran; MeCl** | 7.65 | 0.38 | 10 |
| BlendEI (optimum conc.) | 6.47 | 0.16 | 15 |
| wheat bran | 6.36 | 0.21 | 20 |
| superQ of ground wheat berry | 6.25 | 0.43 | 3 |
| ground brown rice | 6.19 | 0.29 | 4 |
| ground wheat berry | 6.08 | 0.91 | 10 |
| dried hops | 6.04 | 0.45 | 6 |
| wheat germ | 5.70 | 1.03 | 30 |
| cinnamon, TONES, (*Cassia*, freeze-ground) | 5.53 | 1.08 | 10 |
| rice bran | 5.50 | | 2 |
| superQ of wheat germ; MeCl | 4.75 | 1.25 | 3 |
| fresh pears (Bosc) | 4.48 | 1.64 | 10 |
| superQ of TONES cinnamon; MeOH ) | 3.75 | 0.87 | 3 |
| 2-hexanone | 3.63 | 0.22 | 4 |
| hexyl acetate | 3.60 | | 2 |
| superQ of TONES cinnamon; MeCl | 3.50 | 1.09 | 3 |
| ethyl 4-decenoate | 3.50 | 0.25 | 3 |
| turmeric | 3.33 | 0.22 | 3 |
| a-copaene | 3.07 | 0.47 | 7 |
| trans-2-hexen-1-ol | 3.00 | 0.38 | 3 |
| cymene | 3.00 | | 2 |
| myrcene | 2.95 | 0.29 | 5 |
| methyl octanoate | 2.91 | 0.68 | 3 |
| borneol | 2.83 | | 3 |
| ethyl vanillin | 2.63 | 0.44 | 6 |
| all purpose flour | 2.34 | 0.86 | 8 |
| malted barley, grd | 2.13 | | 2 |
| acetone solvent control filter paper | 1.65 | 0.42 | 5 |
| superQ of wheat bran MeOH (after MeCl) | 1.58 | 1.42 | 3 |
| superQ of wheat germ; MeOH | 1.16 | 0.95 | 3 |
| superQ of wheat berry MeOH (after MeCl) | 1.08 | 1.04 | 3 |
| blank filter paper | 1.04 | 0.08 | 6 |
| MeCl solvent control filter paper | 1.00 | 0.01 | 6 |
| MeOH solvent control filter paper | 1.00 | 0.43 | 3 |

*Standard error

Figure 4:
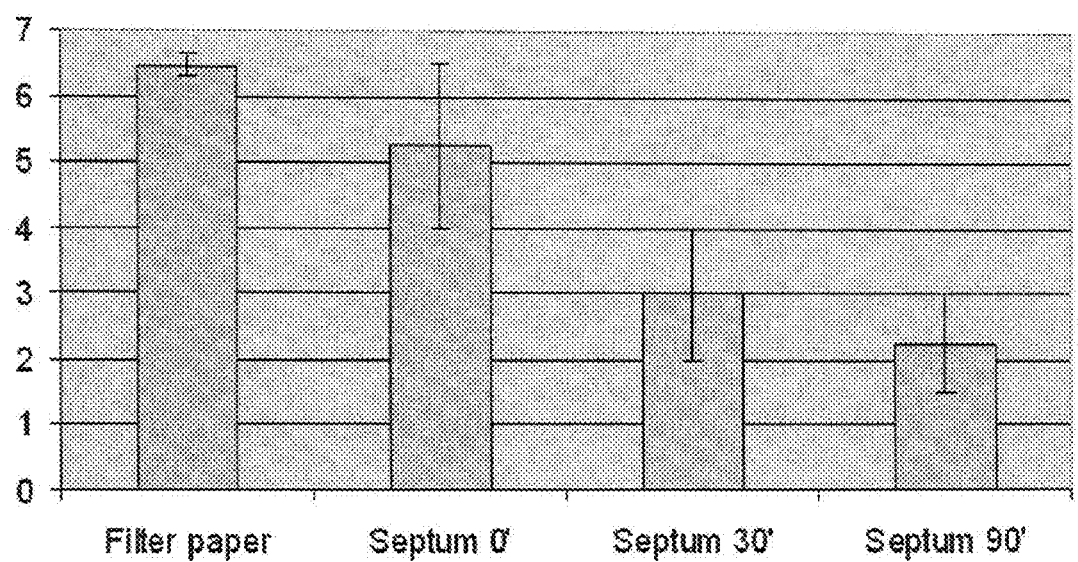
FIG. 4. Attractiveness of septum versus filter paper used as dispensers of the attractant chemicals at 30 minutes, 60 minutes, and 90 minutes after application.

In further tests, BlendEI was applied to red rubber septum to determine how long after application females would still be attracted to the blend. The results are shown in FIG. 4. It was found that a 4× concentration of blend had to be added to the septum to give a score equivalent to filter paper. Thirty minutes after the first test, the septum attractiveness was already significantly degraded (FIG. 4). Septum is allowed to rest 30 minutes before testing.

Conclusion

The inventors' tests indicated that a synthetic chemical mixture that simulates wheat brand volatiles is essentially as attractive to adult female Plodia as wheat brand itself. The mixture includes undecane, hexanal, 1-pentanol, decane, and 2-pentylfuran. In the inventors' tests the mixture was eluted in dichloromethane. The inventors designated the mixture BlendEI. The attraction of BlendEI to female *Plodia* is dependent on dose.

For the foregoing reasons, it is clear that BlendEI provides an innovative insect attractant that may be used in multiple forms and applications. The invention may be modified in multiple ways and applied in various technological applications. The current invention may be modified and customized as required by a specific operation or application to achieve the desired result. Such variations are not to be regarded as a departure from the spirit and scope of the invention, and all such modifications as would be obvious to one skilled in the art are intended to be included within the scope of the following claims.

What is claimed is:

1. A composition comprising a synthetic chemical blend of undecane, hexanal, 1-pentanol, decane, and 2-pentylfuran and optionally a carrier or carrier material.

2. The composition of claim 1 wherein the composition emits vapors comprising undecane, hexanal, 1-pentanol, decane, and 2-pentylfuran.

3. The composition of claim 1 wherein the composition comprises an insect attractant.

4. The composition of claim 3 wherein the insect attractant attracts *Plodia* species.

5. The composition of claim 4 wherein the insect attractant attracts adult female *Plodia*.

6. The composition of claim 1 wherein the composition is comprised of 23.9 ul undecane, 9.61 ul hexanal, 4.09 ul 1-pentanol, 1.78 ul decane, and 1.30 ul 2-pentylfuran.

7. The composition claim 6 wherein the composition in eluted in dichloromethane.

8. The composition of claim 1 wherein the carrier or carrier material acts as a slow release system.

9. A method of attracting *Plodia* species insects, the method comprising treating an area or object with an effective amount of an attractant comprising the composition of claim 1 so that the insects are drawn to the area or object.

* * * * *